US006190383B1

(12) United States Patent
Schmaltz et al.

(10) Patent No.: US 6,190,383 B1
(45) Date of Patent: Feb. 20, 2001

(54) ROTATABLE ELECTRODE DEVICE

(75) Inventors: Dale Schmaltz, Fort Collins; Jenifer Kennedy, Boulder, both of CO (US)

(73) Assignee: Sherwood Services AG, Schaffhausen (CH)

( * ) Notice: Under 35 U.S.C. 154(b), the term of this patent shall be extended for 0 days.

(21) Appl. No.: 09/176,292

(22) Filed: Oct. 21, 1998

(51) Int. Cl.[7] .................................................. A61B 17/32
(52) U.S. Cl. ............................... 606/41; 606/46; 606/48; 606/170; 606/180
(58) Field of Search ................. 606/41, 44, 45, 606/46, 48, 49, 50, 180, 170

(56) References Cited

U.S. PATENT DOCUMENTS

| | | |
|---|---|---|
| 4,355,642 | 10/1982 | Alferness . |
| 4,637,390 * | 1/1987 | Sorochenko ............................. 606/50 |
| 4,637,392 * | 1/1987 | Sorochenko ............................. 606/50 |
| 4,657,017 * | 4/1987 | Sorochenko ............................. 606/50 |
| 4,658,835 | 4/1987 | Pohndorf . |
| 4,711,239 * | 12/1987 | Sorochenko et al. .................. 606/48 |
| 4,827,940 | 5/1989 | Mayer et al. . |
| 5,003,992 | 4/1991 | Holleman et al. . |
| 5,020,545 | 6/1991 | Soukup . |
| 5,085,216 | 2/1992 | Henley, Jr. et al. . |
| 5,122,137 | 6/1992 | Lennox . |
| 5,152,299 | 10/1992 | Soukup . |
| 5,197,964 | 3/1993 | Parins . |
| 5,239,999 | 8/1993 | Imran . |
| 5,242,441 | 9/1993 | Avitall . |
| 5,259,395 | 11/1993 | Li . |
| 5,431,649 | 7/1995 | Mulier et al. . |
| 5,499,981 | 3/1996 | Kordis . |
| 5,507,743 | 4/1996 | Edwards et al. . |
| 5,527,331 * | 6/1996 | Kresch et al. ........................ 606/170 |
| 5,536,267 | 7/1996 | Edwards et al. . |
| 5,609,151 | 3/1997 | Mulier et al. . |
| 5,624,449 | 4/1997 | Pham et al. . |
| 5,630,426 * | 5/1997 | Eggers et al. ........................ 128/734 |
| 5,683,384 | 11/1997 | Gough et al. . |
| 5,697,536 * | 12/1997 | Eggers et al. ........................ 604/114 |
| 5,697,909 | 12/1997 | Eggers et al. . |
| 5,697,925 | 12/1997 | Taylor . |
| 5,810,809 * | 9/1998 | Rydell .................................... 606/49 |
| 5,904,681 * | 5/1999 | West, Jr. ................................ 606/41 |
| 5,921,982 * | 7/1999 | Lesh et al. ............................. 606/41 |
| 5,941,876 * | 8/1999 | Nardella et al. ...................... 606/45 |

* cited by examiner

Primary Examiner—Linda C. M. Dvorak
Assistant Examiner—David M. Ruddy

(57) ABSTRACT

An apparatus for thermal treatment of a tissue mass having an elongated housing having a proximal and a distal end and defining a longitudinal axis, and further including at least two electrodes supported at its distal end and mounted for rotation to facilitate entry and passage through a tissue mass. A drive shaft may be disposed within the elongated housing and operatively engageable with the electrodes for causing their rotational movement. The apparatus may include an electrode gear and a drive shaft gear in cooperative engagement whereby rotation of the drive shaft causes corresponding rotation of the electrodes. Preferably, a motor is operatively connected to the drive shaft causing its rotational movement. Desirably, the distal end of the electrodes are threaded. A method for thermally treating a tissue mass is disclosed.

26 Claims, 5 Drawing Sheets

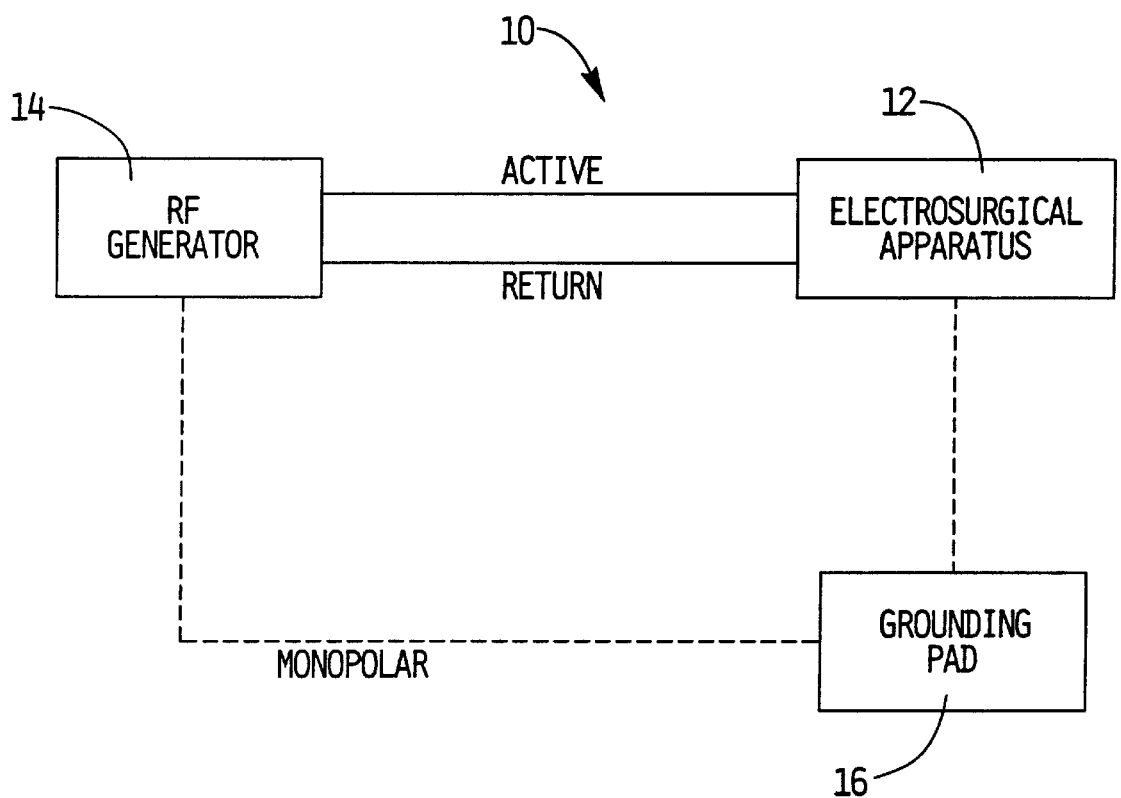
FIG_1

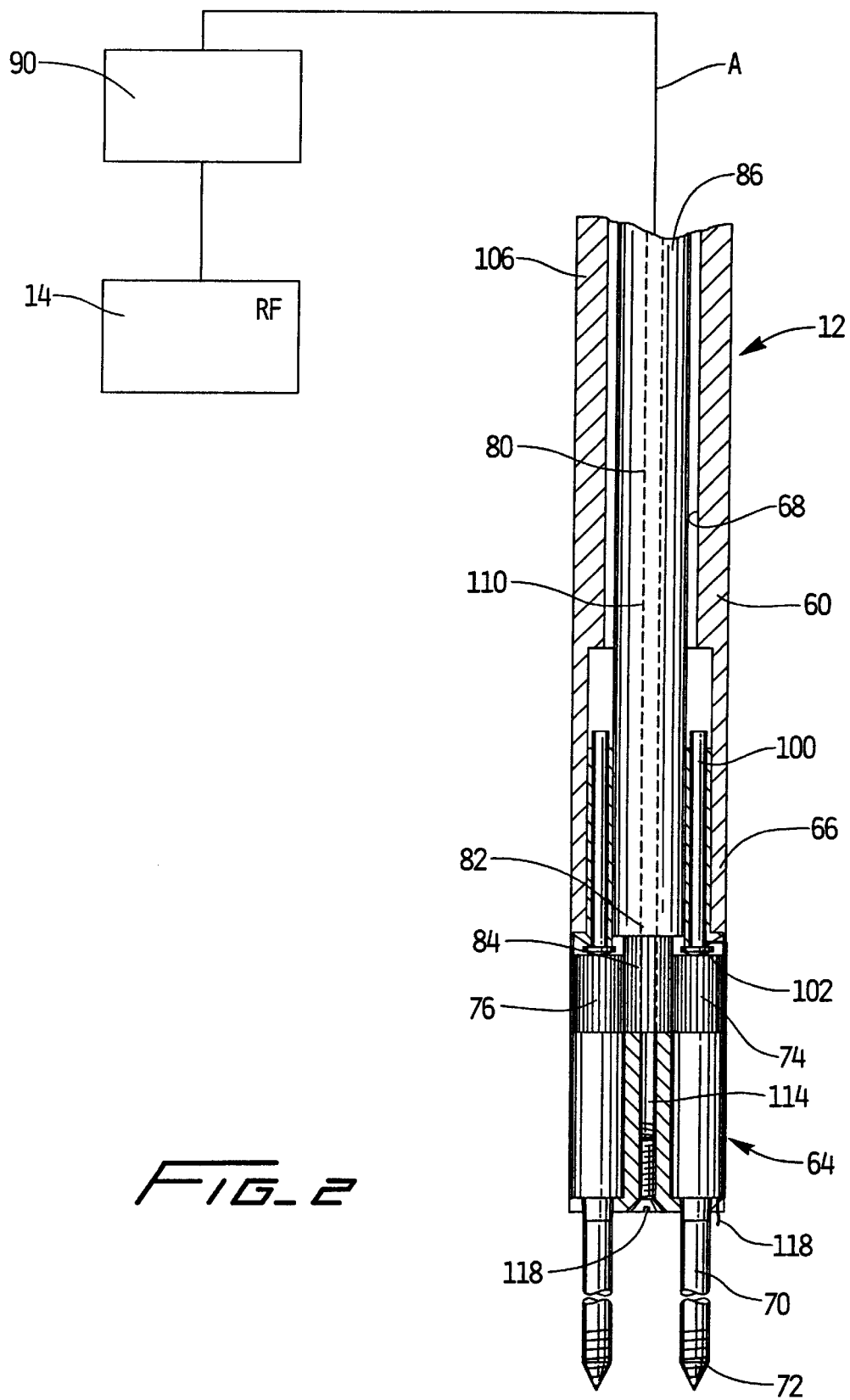

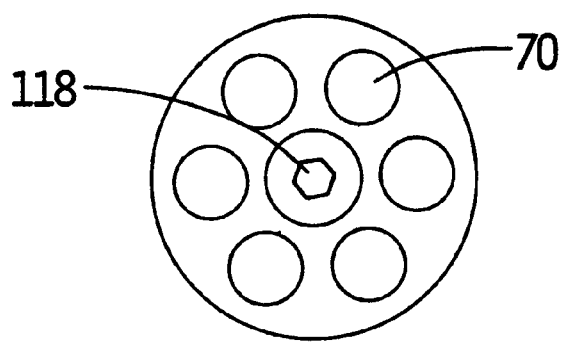
FIG_3
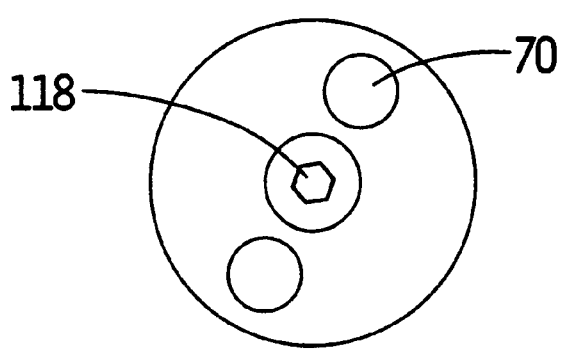
FIG_5

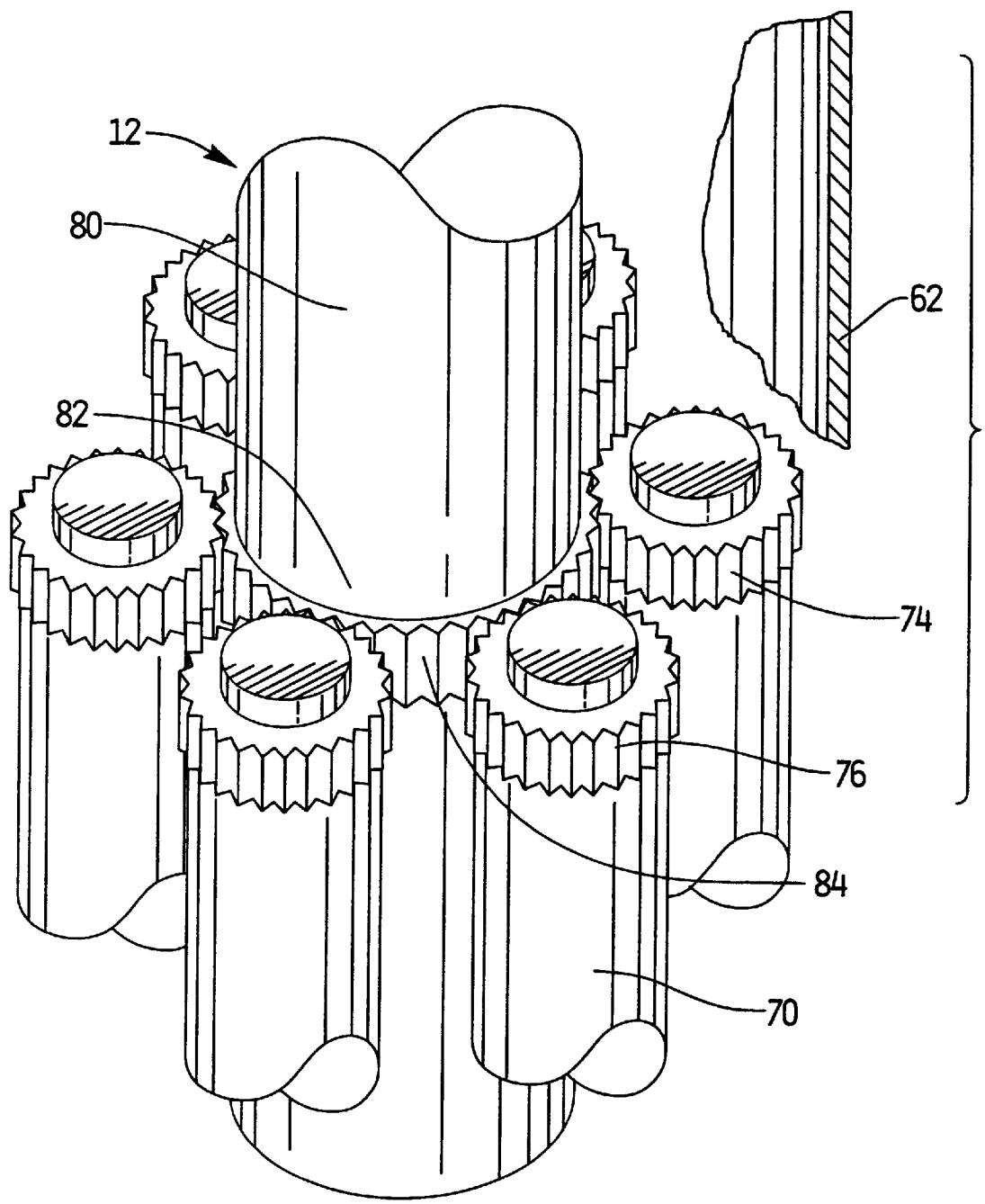
FIG_4

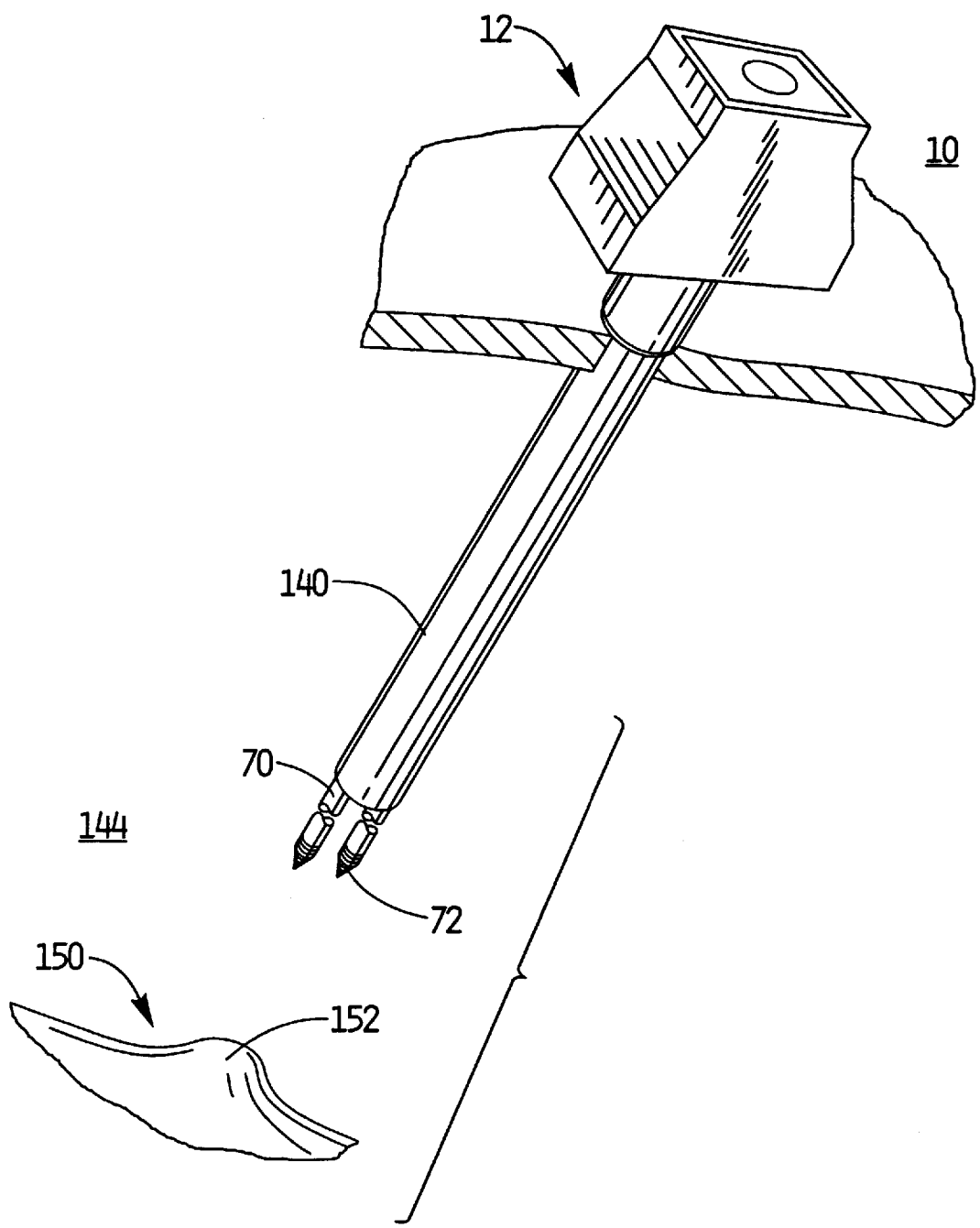
FIG_6

ROTATABLE ELECTRODE DEVICE

BACKGROUND

1. Technical Field

The present disclosure relates to an apparatus and method for thermal treatment of a tissue mass with radio frequency (RF) energy. In particular, the present disclosure relates to an apparatus for minimally invasive treatment of intramural leiomyomas.

2. Description of the Related Art

Myomas are currently the leading indication for surgery in women. A myoma is composed of muscle tissue. In women, a tumor of the uterus is a leiomyoma and may also be called a fibroid. Uterine leiomyomas are typically benign tumors located in the muscular layer of the uterus. These tumors affect 20–30% of women during their reproductive years. The highest rate of leiomyomas occur during the fifth decade of a woman's life. Depending on their size and location, leiomyomas can be asymptomatic or they can cause pelvic pain, dyspareunia, urinary problems or menorrhagia.

Currently, there are four types of therapy available to relieve a patient's symptoms due to a myoma: medical management, hysterectomy, myomectomy and myolysis. Medical management is the administration of hormone therapy which shrinks the myoma by inhibiting estrogen production. The disadvantages are adverse side affects and cost.

A hysterectomy involves the total removal of the uterus which can be performed by a variety of methods including laparotomy and vaginal or laparoscopic assisted vaginal hysterectomy (LAVH). The disadvantages of a hysterectomy are the elimination of fertility, long recovery period, early ovarian failure, urinary symptoms, fatigue, changes in sexual interest and function, depression, surgical complications, increase in the probability of developing cardiovascular disease and psychological loss of full womanhood.

A myomectomy procedure includes the removal of a myomatous tumor from the uterine wall. The disadvantages of the myomectomy procedure include treatment complexity in infertility, blood loss, time consumption and long postoperative care. Other complications include uterine perforation, delusional hyponoctrimia and thermos injury.

The above-mentioned invasive procedures for treatment of tumors are extremely disruptive and may cause damage to healthy tissue. For example, during the invasive surgical procedure, a physician must exercise care in not cutting the tumor in a manner that creates seeding of the tumor, which may result in metastasis. In recent years, product development has been directed towards minimizing the traumatic nature of traditional invasive surgical procedures by using non-invasive procedures.

A current non-invasive procedure is myolysis which reduces a myoma tumor mass by applying an electrosurgical cutting wave form with bipolar needles. Bipolar needles transfer localized current to the tissue between the needles. The thermal energy induced by the intrinsic effect of electric current necroses tumor tissue, denatures proteins and destroys vascularity of the myoma tissue. Subsequently, the myoma mass will atrophy if treatment is sufficient throughout.

Ideally, the clinical symptoms recede allowing a patient to return to normal activities. The benefits of myolysis include the advantages of laparoscopic surgery and further include absence of regrowth of the myoma tissue, minimized blood loss, preservation of the uterus, and a 41% reduction of tumor volume and reduction of adhesion formation compared to a myomectomy.

Myolysis may be accomplished either by laparoscopic methods or by endoscopic methods, such as transvaginal. The laparoscopic methods involve use of a cannula through which a myolysis tool may be introduced. The transvaginal approach may be through the cervix or through the fornix.

The presently available myolysis devices suffer from various drawbacks and disadvantages. For instance, sticking the electrodes into a myoma may cause trauma to the uterus upon penetration attempts into the myoma. This is particularly true in the single or dual bipolar needle devices which require multiple penetrations into tissue for complete ablation. U.S. Pat. No. 5,630,426 discloses single and dual bipolar needle devices for necrosis of a tumor.

An article by Dr. Herbert Goldfarb "*Bipolar Laparoscopic Needles for Myoma Coagulation,*" *The Journal of the American Assoc. of Gynecologic Laparoscopis*, February. 1995, reports that an average of thirty to fifty passes into different areas of a myoma with the bipolar needle is required in order to achieve complete tissue necrosis. Further, trauma is increased upon retraction of the device due to needle adhesion or sticking to surrounding structures and tissue. Additionally, needle devices of the prior art which rely on puncture-like penetration for insertion are known to deform because of the hard physical properties of a myoma.

Multiple needle devices are known for reducing the number of penetrations required for complete ablation of a tumor mass. U.S. Pat. No. 5,536,267 defines an apparatus that surrounds a tumor with a plurality of needle electrodes and defines an ablative volume. The '267 device, however, may pose a risk of damage or adhesions to surrounding structures because of the puncture-like penetration of the needles. This multiple needle approach has the disadvantage of moving the tissue mass upon insertion thereby affecting surrounding structures and tissue. Further, withdrawal of the needle electrodes from the desiccated tissue may pull on surrounding structures and healthy tissue causing damage thereto. Additionally, U.S. Pat. No. 5,697,909 discloses an electrosurgical probe having an array of isolated electrode terminals for treating structures within a body.

Accordingly, there is a present need in the state of the art for a needle electrode device that reduces the number of needle electrode penetrations required to ablate a tissue mass such as a myoma and further reduces the risk of damage or adhesions to surrounding healthy tissue and structures during needle electrode insertion and retraction. In the treatment of myomas, it is desirable that such a device reduces the risk of perforation of the uterus and damage to the serosa layer. Moreover, prevention of charring of tissue and tissue sticking to the needle electrode during coagulation, improved deployment into a tissue mass, minimized blood loss and speed of procedure are also desired.

SUMMARY

Generally speaking, the present disclosure is directed to an apparatus for the thermal treatment of tissue. The apparatus has particular application in the treatment of myomas although other uses for the apparatus are envisioned.

The apparatus advantageously reduces the number of electrode penetrations thereby substantially reducing the risk of damage or adhesions to surrounding healthy. tissue or structures during electrode insertion and retraction. In a preferred embodiment, the apparatus includes an elongated housing having a proximal end and a distal end and defining a longitudinal axis. At least two electrodes are supported at the distal end of the elongated housing. The electrodes are mounted for rotation to facilitate entry and passage through tissue. The electrodes may include an external threaded portion dimensioned to facilitate advancement and retention of the electrode in the tissue. The threaded portion also increases the effective surface treatment areas of the electrodes thereby providing increased necrosis volume.

Desirably, the apparatus includes a shaft disposed in the elongated housing and operatively engageable with the electrodes. The shaft is mounted for movement relative to the elongated housing to cause electrode rotation. Preferably, each of the electrodes has an electrode gear and the shaft also has a gear. The gears are in cooperative engagement whereby rotation of the shaft causes corresponding rotation of the electrodes. In one embodiment, a motor is operatively connected to the shaft to cause rotational movement of the shaft. Alternatively, the shaft may be manually rotated.

In a preferred embodiment, the apparatus includes a plurality of needle electrodes supported at the distal end of the elongated housing. Desirably, the needle electrodes are RF electrodes and are connected to a RF power source.

A method using the apparatus is disclosed. The method has application in the treatment of benign uterine fibroids and for bipolar myoma coagulation. The method includes the steps of positioning the apparatus adjacent to the surface of a myoma, rotating the needle electrodes to advance the needle electrodes to a position adjacent the myoma center and energizing the electrode needles with electrosurgical energy. Preferably, the needle electrodes are constantly or intermittently irrigated during insertion and retraction of the device. An irrigation step to suppress smoke formation and prevent buildup of eschar on the needle electrodes is also envisioned. In addition, bleeding may be controlled by injecting a coagulant during a coagulating step.

The apparatus and method for use thereof, provides a high level of control for a surgeon due to rotation of the needle electrodes resulting in a low axial force on the tissue mass during electrode insertion and retraction. The low axial force improves stability and control during insertion and the screw or rotating action allows the electrode to quickly attach to the tissue mass and thereby prevent it from slipping off to one side. During retraction, the high level of control afforded the surgeon reduces the risk of disturbing surrounding structures.

BRIEF DESCRIPTION OF THE DRAWINGS

Various preferred embodiment(s) of the present disclosure are described herein, with reference to the drawings, wherein:

FIG. 1 is a schematic view of the electrosurgical system in accordance with the principles of the present disclosure;

FIG. 2 is a cross-sectional view of the electrosurgical apparatus of the system of FIG. 1;

FIG. 3 is an axial view of the distal end of the electrosurgical apparatus;

FIG. 4 is a view illustrating the gear arrangement for connecting the drive shaft and electrodes of the electrosurgical apparatus;

FIG. 5 is an axial view of an alternate embodiment of an electrosurgical apparatus including two electrodes; and FIG. 6 is a view illustrating insertion of the electrosurgical apparatus through a trocar for treating a myoma site.

DETAILED DESCRIPTION OF THE PREFERRED EMBODIMENTS

In accordance with the present disclosure, referring now in detail to the drawings wherein like reference numerals identify similar or like components throughout the several views, FIG. 1 illustrates, in schematic view, the system in accordance with the principals of the present disclosure. System 10 generally includes electrosurgical apparatus 12 and power generator 14 electrically connected to apparatus 12. Power generator 14 is a radio-frequency generator providing RF energy, typically, in the range of about 0.1–1.0 MHZ. Power generator 14 may be any commercially available generator suitable to desiccate, coagulate and cause ablation of a tissue mass for the purpose of electrosurgical necrosis.

System 10 may operate in monopolar mode or bipolar mode. When in the monopolar mode, apparatus 12 and power generator 14 are used in conjunction with a grounding pad 16 (shown in phantom in FIG. 1) as is conventional in the art. For most applications, however, system 10 is used in the bipolar mode as will be discussed hereinbelow.

Referring to FIG. 2, various features of the electrosurgical apparatus 12 will now be described. Electrosurgical apparatus 12 includes an elongated housing 60 having a sleeve member 62 and a needle support 64 mounted to a distal end 66 of sleeve member 62. Sleeve member 62 has a longitudinal bore 68 extending the length thereof and defines a longitudinal axis A—A. Needle support 64 functions in supporting a plurality of electrodes 70 which are adapted for rotational movement within needle support 64. Needle support 64 may be connected to sleeve member 66 by any conventional means including adhesives, snap-lock fit, bayonet coupling, etc. In the alternative, sleeve member 62 and needle support 64 may be a single monolithically formed component.

In the preferred embodiment, electrosurgical apparatus 12 includes six (6) electrodes 70 (FIG. 3) supported within needle support 64 and positioned circumferentially about elongated housing 60 in equidistant relation. In an alternate embodiment, illustrated in FIG. 5, electrosurgical apparatus 12 includes two (2) electrodes supported within needle support 64. Referring back now to FIG. 2, each electrode 70 is preferably a needle electrode, i.e., possessing a sharpened distal end to facilitate penetration through tissue. In addition, each electrode 70 includes a threaded portion 72, shown schematically in FIG. 2. Threaded portion 72 of electrode 70 provides significant advantages including: 1) facilitating entry and retention of electrode 70 within a tissue mass (not shown); 2) facilitating exit of electrode 70 from the tissue mass subsequent to the procedure; and 3) increasing effective surface treatment area of electrode 70 thereby enhancing necrosis volume potential. In addition, each electrode 70 has a proximal end 74 defining a gear 76, preferably a spur gear, the significance of which is discussed hereinabove.

As best illustrated in FIG. 4, in conjunction with FIG. 2, electrosurgical apparatus 12 further includes a drive shaft 80 mounted for rotational movement within sleeve member 62. A distal end 82 of drive shaft 80 includes a shaft gear 84, preferably, a pinion gear, which merges with electrode gears 76 whereby rotation of drive shaft 80 causes corresponding rotational movement of electrodes 70 through the cooperating action of the respective gears.

Referring back now to FIG. 2, drive motor 90 is operatively connected to drive shaft 80 to supply the forces necessary to rotate drive shaft 80 and electrodes 70 at a sufficient velocity to enter the tissue mass. Alternatively, it is envisioned that drive shaft 80 may be rotated manually via manual engagement with a handle mounted on proximal end 86 of drive shaft 80.

With reference to FIG. 2, electrosurgical apparatus 12 further includes a plurality of thrust bearing pins 100 disposed within sleeve member 62 adjacent electrodes 70. The number of thrust bearing pins 100 corresponds to the number of electrodes 70, e.g., six. Thrust bearing pins 100 each define an enlarged head 102 which contacts a surface of proximal end 74 of each electrode 70. Thrust bearing pins 100 function to absorb or counter the thrust load of each electrode 70 during rotation and entry into tissue. Thrust bearing pins 100 also serve as the electrical connection between power generator 14 and electrode 70. In particular, thrust bearing pins 100 are in electrical connection with power generator 14 through electrical wires (not shown) which may, e.g., extend through longitudinal openings or passageways in the outer wall 106 of sleeve member 62 and attach to proximal end of each thrust bearing pin 100.

Electrosurgical apparatus 12 may include a conduit or passageway for the introduction of irrigation fluid to the treatment site. Preferably, as shown in FIG. 2, drive shaft 80 includes a central passage 110 which fluidly connects with a fluid channel 114 in needle support 64. The conduit or passageway terminates in a fluid port 118. (See also FIG. 3) The irrigation fluid suppresses smoke formation and prevents buildup of eschar on electrodes 70.

The operation of the electrosurgical apparatus 12 for treating a dense tissue mass, in particular, a myoma, to apply electrosurgical energy to the myoma to cause necrosis thereof will be described. With reference to FIG. 6, a body cavity 144 is insufflated with insufflation gases as is conventional with laparoscopic surgical techniques. Thereafter, a trocar 140 is advanced through the body cavity wall and within body cavity 144 to a position adjacent the targeted site. Electrosurgical apparatus 12 is inserted within trocar 140 and advanced such that needle electrodes 70 are in contacting engagement with the tissue mass, e.g., myoma 150.

Motor 90 is then causing rotation of drive shaft 80 and needle electrodes 70, and advancement of the needle electrodes 70 within myoma 150 and adjacent to myoma center 152. An axial force may be applied by the surgeon to electrosurgical apparatus 12 to facilitate insertion within myoma 150. It is to be appreciated that threaded portion 72 of each needle electrodes 70 facilitates advancement and retention of the needle electrodes 70 within myoma 150 as discussed above.

Motor 90 is deactivated. RF generator 14 is energized to energize electrodes 70 to treat myoma 150 with electrosurgical energy. In a bipolar mode of electrosurgical generator 14, RF energy is transmitted between the (6) needle electrode 70 arrangement to define a treatment volume which encompasses a relatively large volume of tissue. Moreover, the effective treatment volume of the electrodes is further increased through the enhanced electrode surface area as provided through the threaded configuration discussed hereinabove. Accordingly, these improvements provided by the multiple electrode arrangement (e.g., the six (6) electrode arrangement) and the threaded configuration enhance the tissue volume treatment area, thereby minimizing the need for multiple insertions of needle electrodes 70. Similarly, in a monopolar mode, the multiple electrode arrangement provides advantages with respect to enhanced treatment volume of the electrosurgical apparatus 12.

Preferably, necrosis is performed for approximately 8 to 10 seconds. During treatment, constant or intermittent irrigation of needle electrodes 70 from fluid port 118 of system 10 may be applied during penetration and retraction of electrosurgical apparatus 12 to suppress smoke formation and prevents buildup of eschar on needle electrodes 70. A coagulant may be provided during use of electrosurgical apparatus 12 to prevent excessive bleeding.

After necrosis of myoma 150 is complete, motor 90 may cause reverse rotation of drive shaft 80, and corresponding reverse rotation of needle electrodes 70, causing them to rotate and release from myoma 150.

It will be understood that various modifications may be made to the embodiment disclosed herein. For example, while specific preferred embodiments of the electrosurgical apparatus have been described in detail, structures that perform substantially the same function in substantially the same way to achieve the same result may also be used. For example, the electrodes may be in a banked or alternating arrangement. Further, the exposed portion of the electrodes may be retractable within the main housing. Therefore, the above description should not be construed as limiting, but merely as exemplifications of preferred embodiments. Those skilled in the art will envision other modifications within the scope and spirit of the present disclosure.

What is claimed is:

1. An electrosurgical apparatus for thermal treatment of a tissue mass comprising:
    an elongated housing having proximal and distal ends, and defining a longitudinal axis;
    at least two electrodes supported at the distal end of the elongated housing, the electrodes mounted for rotation to facilitate entry and passage through tissue and each having a distal end forming a substantially pointed tip with a conductive portion on a surface thereof; and
    an RF energy source in electrical connection to the electrodes to supply radio frequency energy.

2. The apparatus according to claim 1, wherein at least one of the electrodes includes an external threaded portion dimensioned to facilitate retention of the one electrode in the tissue.

3. The apparatus according to claim 2, wherein each of the electrodes includes an external threaded portion dimensioned to facilitate retention of the electrodes in the tissue.

4. The apparatus according to claim 1, further including a drive shaft disposed in the elongated housing and operatively engageable with the electrodes, the drive shaft mounted for movement relative to the elongated housing to cause rotation of the electrodes.

5. The apparatus according to claim 4, wherein the drive shaft is adapted for rotation within the elongated housing.

6. The apparatus according to claim 5, wherein each of the electrodes has an electrode gear associated therewith and the drive shaft has a drive shaft gear associated therewith in engagement with the electrode gears, whereby rotation of the drive shaft causes corresponding rotation of the electrodes.

7. The apparatus according to claim 4, further including a motor operatively connected to the drive shaft to cause rotation of the drive shaft.

8. The apparatus according to claim 1, wherein there are six electrodes supported at the distal end of the elongated housing.

9. An electrosurgical apparatus for thermal treatment of a tissue mass comprising:
    an elongated housing having proximal and distal ends, and defining a longitudinal axis;
    at least three electrodes supported at the distal end of the elongated housing, the electrodes mounted for rotation to facilitate entry and passage through tissue; and an RF energy source in electrical connection to the electrodes to supply radio frequency energy.

10. The apparatus according to claim 1, wherein the electrodes are radio frequency (RF) electrodes.

11. The apparatus according to claim 10, further including a radio frequency (RF) power source connected to the electrodes for supplying radio-frequency (RF) current.

12. The apparatus according to claim 9, wherein the at least three electrodes have an external threaded portion dimensioned to facilitate retention of the at least three electrodes in the tissue.

13. The apparatus according to claim 9, further including a drive shaft disposed in the elongated housing and operatively engageable with the electrodes, the drive shaft mounted for movement relative to the elongated housing to cause rotation of the electrodes.

14. The apparatus according to claim 9, wherein there are six electrodes supported at the distal end of the elongated housing.

15. An electrosurgical apparatus for thermal treatment of a tissue mass comprising:
   a rotatable elongated drive shaft having a proximal end, a distal end and defining a longitudinal axis;
   an actuator for cooperatively engaging the drive shaft, whereby the actuator causes rotation of the drive shaft;
   a plurality of electrodes, each of the electrodes having a proximal end and an independent conductors distal end forming a substantially pointed tip with a conductive portion on a surface thereof, and a length therebetween defining a longitudinal axis, wherein the plurality of independent conductors are supported adjacent the distal end of the drive shaft and the proximal end of each of the electrodes is adapted for engaging the distal end of the drive shaft, the drive shaft causing rotation of the plurality of electrodes to facilitate entry and passage through tissue; and
   an RF energy source in electrical connection to the independent conductors to supply radio frequency energy.

16. The apparatus according to claim 15, further including an elongated housing having a proximal end, a distal end and defining a longitudinal axis, the elongated housing accommodating at least a portion of the drive shaft, and
   the plurality of electrodes mounted at the distal end of the elongated housing and the drive shaft is disposed within the elongated housing and mounted for rotation therewithin.

17. The apparatus according to claim 15 further including an end cap mounted to the distal end of the elongated housing, the end cap defining openings for receipt of the plurality of electrodes.

18. The apparatus according to claim 15, wherein the actuator comprises a motor.

19. The apparatus according to claim 15, wherein the drive shaft comprises a drive shaft gear and each of the electrodes comprises an electrode gear in engagement with the drive shaft gear whereby rotation of the drive shaft causes corresponding rotation of the electrodes.

20. The apparatus according to claim 15, wherein the distal end of each of the plurality of electrodes includes a threaded portion to facilitate retention of the plurality of electrodes in the tissue.

21. The apparatus according to claim 15, wherein the plurality of electrodes are retractable from the tissue mass.

22. The apparatus according to claim 15, wherein the actuator is adapted to cause rotation in a reverse direction for retracting the plurality of electrodes from the tissue.

23. A method for thermal treatment of a tissue mass comprising the steps of:
   providing an electrosurgical device having at least two rotatable electrodes, each of the electrodes having a distal end forming a substantially pointed tip with a conductive portion on a surface thereof;
   positioning the at least two rotatable electrodes adjacent tissue;
   rotating the at least two electrodes to cause penetration within the tissue; and
   supplying electrosurgical energy to at least two electrodes sufficient to treat the tissue.

24. The method according to claim 23, further including a step of retracting the electrosurgical device from tissue by reversing rotation of each of the electrodes.

25. The method according to claim 23, wherein the first and second electrodes each include external threaded portions and wherein during the step of rotating the threaded portions engage the tissue to facilitate advancement therein.

26. The method according to claim 23, further including a step of irrigating the treated tissue and adjacent tissue.

* * * * *